(12) United States Patent
Chen et al.

(10) Patent No.: US 12,169,191 B2
(45) Date of Patent: Dec. 17, 2024

(54) OPTICAL WATER QUALITY DETECTION DEVICE WITH EXAMINING PROPERTY PROBE

(71) Applicant: Taiwan RedEye Biomedical Inc., Hsinchu (TW)

(72) Inventors: Yu-Hsun Chen, Hsinchu (TW); I-Hua Wang, Hsinchu (TW); Shuo-Ting Yan, Hsinchu (TW)

(73) Assignee: Taiwan RedEye Biomedical Inc., Hsinchu (TW)

( * ) Notice: Subject to any disclaimer, the term of this patent is extended or adjusted under 35 U.S.C. 154(b) by 260 days.

(21) Appl. No.: 17/847,387

(22) Filed: Jun. 23, 2022

(65) Prior Publication Data

US 2023/0417723 A1    Dec. 28, 2023

(51) Int. Cl.
*G01N 33/18* (2006.01)
*G01N 21/85* (2006.01)

(52) U.S. Cl.
CPC ..... *G01N 33/1886* (2013.01); *G01N 21/8507* (2013.01)

(58) Field of Classification Search
None
See application file for complete search history.

(56) References Cited

U.S. PATENT DOCUMENTS

| 5,402,241 A * | 3/1995 | Jeannotte | G01N 21/83 250/576 |
| 7,349,092 B1 * | 3/2008 | Tiwald | G01N 21/0303 356/135 |
| 2006/0078961 A1 * | 4/2006 | Chiu | B01L 3/502715 435/288.5 |
| 2006/0234298 A1 * | 10/2006 | Chiu | G01N 29/022 435/7.1 |
| 2018/0128937 A1 * | 5/2018 | Donzier | E21B 49/08 |

* cited by examiner

*Primary Examiner* — Brandi N Hopkins
*Assistant Examiner* — Nigel H Plumb
(74) *Attorney, Agent, or Firm* — BACON&THOMAS,PLLC (57) ABSTRACT

An optical water quality detection device with an examining property probe, which includes two stationary seats and a fencing frame. The fencing frame is detachably mounted in a detecting channel between the two stationary seats and has a guiding protrusion and two elongated orifices. The guiding protrusion protrudes from an inner side of an upper portion of the fencing frame and has a convex surface. The convex surface extends along a cycloidal path. The two elongated orifices are formed through the two side panels respectively and extend to the bottom panel. The cycloidal path on the convex surface in the fencing frame, with its structural design, assists in guiding the air bubbles stuck in the detecting channel to leave the detecting channel without vibrating the examining property probe. Since the air bubbles do not remain in the detecting channel, the spectral information is not affected.

15 Claims, 6 Drawing Sheets

OPTICAL WATER QUALITY DETECTION DEVICE WITH EXAMINING PROPERTY PROBE

BACKGROUND OF THE INVENTION

1. Field of the Invention

The present invention relates to an optical water quality detection device for examining property of water, especially to an optical water quality detection device with an examining property probe.

2. Description of the Prior Art(s)

An optical water quality detection device, such as a urine analyzers, a PH meter, a hemoglobin detecting device, a pesticide residue detector and the like, is used for detecting composition of aqueous solutions and has a light source module and a spectrophotometer. The light source module on one side of the optical water quality detection device emits a light beam to the aqueous solution and the spectrophotometer on the other side of the optical water quality detection device receives the light beam that passes through the aqueous solution. The spectrophotometer is used to measure intensity of a light beam at different wavelengths. Different spectrophotometers may be used for detecting different wavelength ranges of lights. As the light beam for detection is received, a spectral information is generated. The spectral information records the wavelength and the intensity of the light beam. Since different components in the aqueous solution have different absorption capacities for lights of different wavelengths in the light beam, concentration of a specific component in the aqueous solution can be obtained by analyzing the spectral information.

A conventional optical water quality detection device for easy use has a detecting probe mounted to a detecting end of the conventional optical water quality detection device. A light source module and a spectrophotometer are mounted in the detecting probe, and a detecting channel is formed between the light source module and the spectrophotometer for aqueous solution to be detected flowing between the light source module and the spectrophotometer.

However, when putting the convention optical water quality detection device from air into the aqueous solution to be detected, air bubbles would be formed easily. If the air bubbles are stuck in the detecting channel, the resulting spectral information would be affected, causing misjudgement of the components in the aqueous solution. Generally, air bubbles in fluid can be eliminated by vibration. In addition to encouraging the air bubbles to flow upward and be expelled from the fluid, said vibration also encourages small bubbles to aggregate into large bubbles. Thus, the large bubbles with larger buoyance flow upward naturally and are expelled from the liquid. However, said vibration would cause adverse effects, such as structural loosening and short circuits, on optical elements in the conventional optical water quality detection device. Therefore, it is not suitable to eliminate the air bubbles in conventional optical water quality detection device by vibration.

To overcome the shortcomings, the present invention provides an optical water quality detection device with an examining property probe to mitigate or obviate the aforementioned problems.

SUMMARY OF THE INVENTION

The main objective of the present invention is to provide an optical water quality detection device with an examining property probe. The examining property probe includes two stationary seats and a fencing frame.

The two stationary seats are connected with each other. Each of the stationary seats has an inner sidewall. The inner sidewalls of the two stationary seats face toward each other and are disposed apart from each other. A detecting channel is formed between the inner sidewalls of the two stationary seats.

The fencing frame is annular, is detachably mounted in the detecting channel between the two stationary seats, and has a guiding protrusion and two elongated orifices. The guiding protrusion protrudes from an inner side of an upper portion of the fencing frame and has a convex surface. The convex surface extends between the two side panels along a cycloidal path and has two opposite end edges connected with the two side panels respectively. The two elongated orifices are formed through the two side panels respectively and extend to the bottom panel. Each of the elongated orifices has an upper end connected with a respective one of the end edges of the convex surface of the guiding portion.

The cycloidal path on the convex surface in the fencing frame, with its structural design, assists in guiding the air bubbles stuck in the detecting channel to leave the detecting channel without vibrating the examining property probe. Since the air bubbles do not remain in the detecting channel, the spectral information is not affected.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
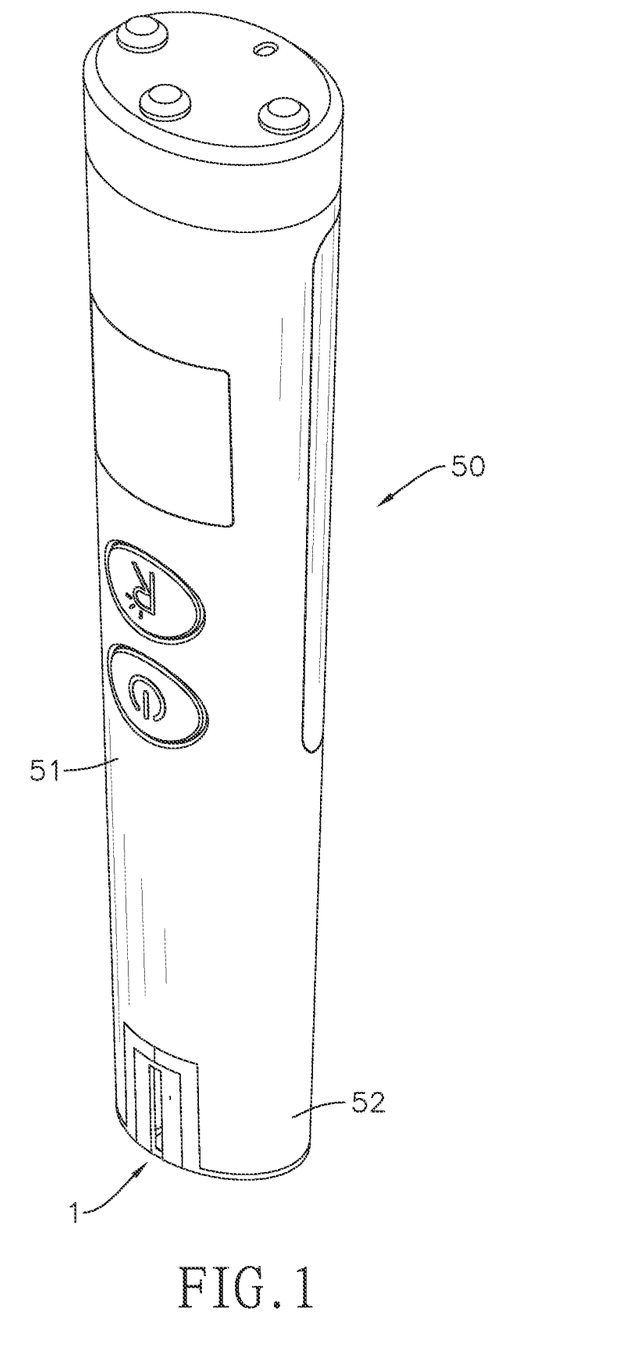
FIG. 1 is a perspective view of an optical water quality detection device with an examining property probe in accordance with the present invention.

With reference to FIG. 1, an examining property probe 1 of an optical water quality detection device 50 in accordance with the present invention is mounted to a detecting end 52 of a waterproof housing 51 of the optical water quality detection device 50.

Figure 2:
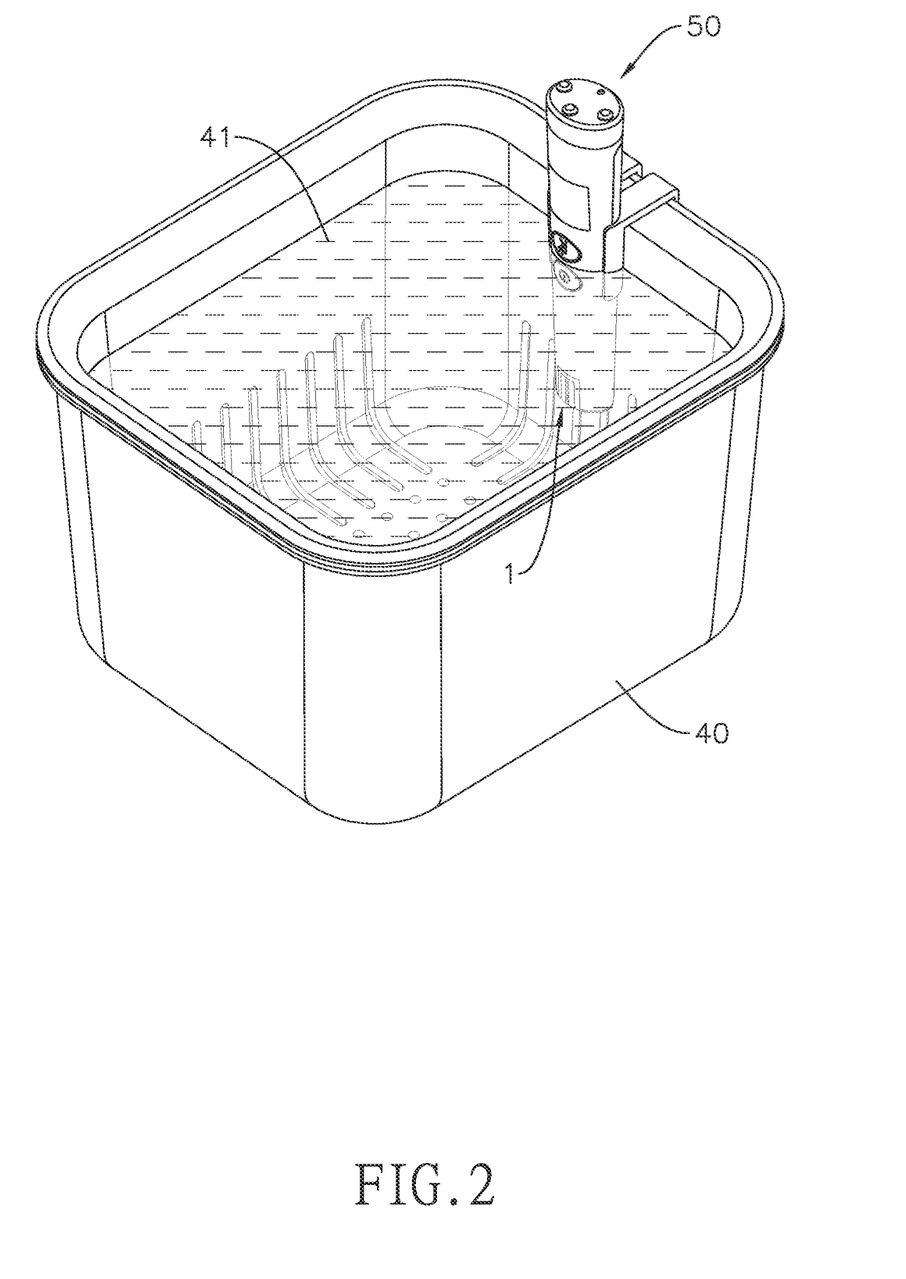
FIG. 2 is an operational perspective view of the optical water quality detection device in FIG. 1.

With further reference to FIG. 2, take the detection of residual pesticides in water for example. When in use, the optical water quality detection device is put in a container 40, which can be any bucket used for washing vegetables and fruits. When rinsing the vegetables and fruits in the container 40 with liquid 41, which is usually tap water, to dilute the residual pesticides on the vegetables and fruits, the optical water quality detection device is immersed in the liquid 41 to continuously monitor concentration of the pesticides dissolved into the liquid 41, so as to timely and directly show the pesticide residue status on the vegetables and fruits to users.

Figure 3:
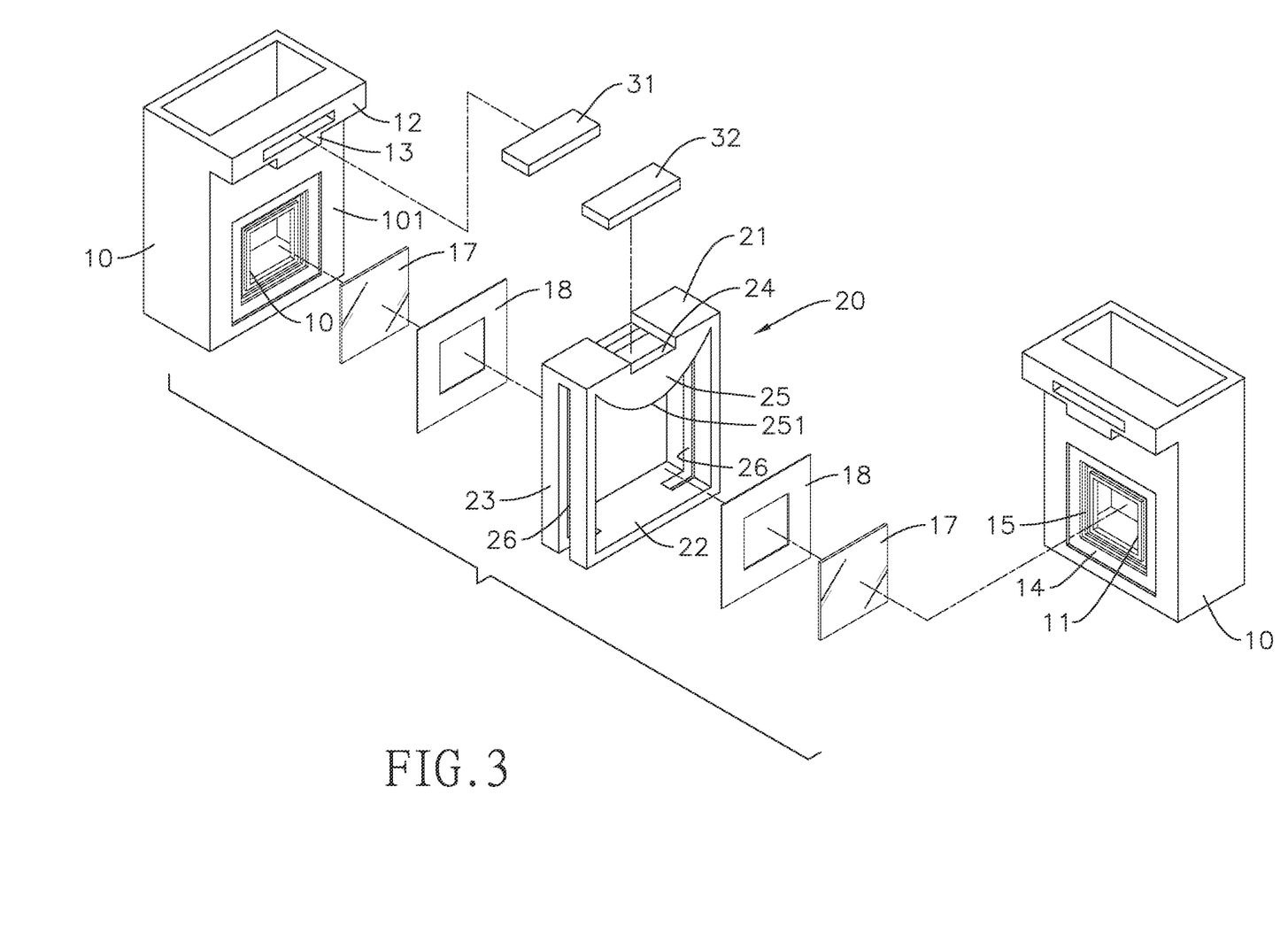
FIG. 3 is an exploded perspective view of the examining property probe in FIG. 1.

With further reference to FIG. 3, the examining property probe 1 comprises two stationary seats 10 and a fencing frame 20.

Figure 6:
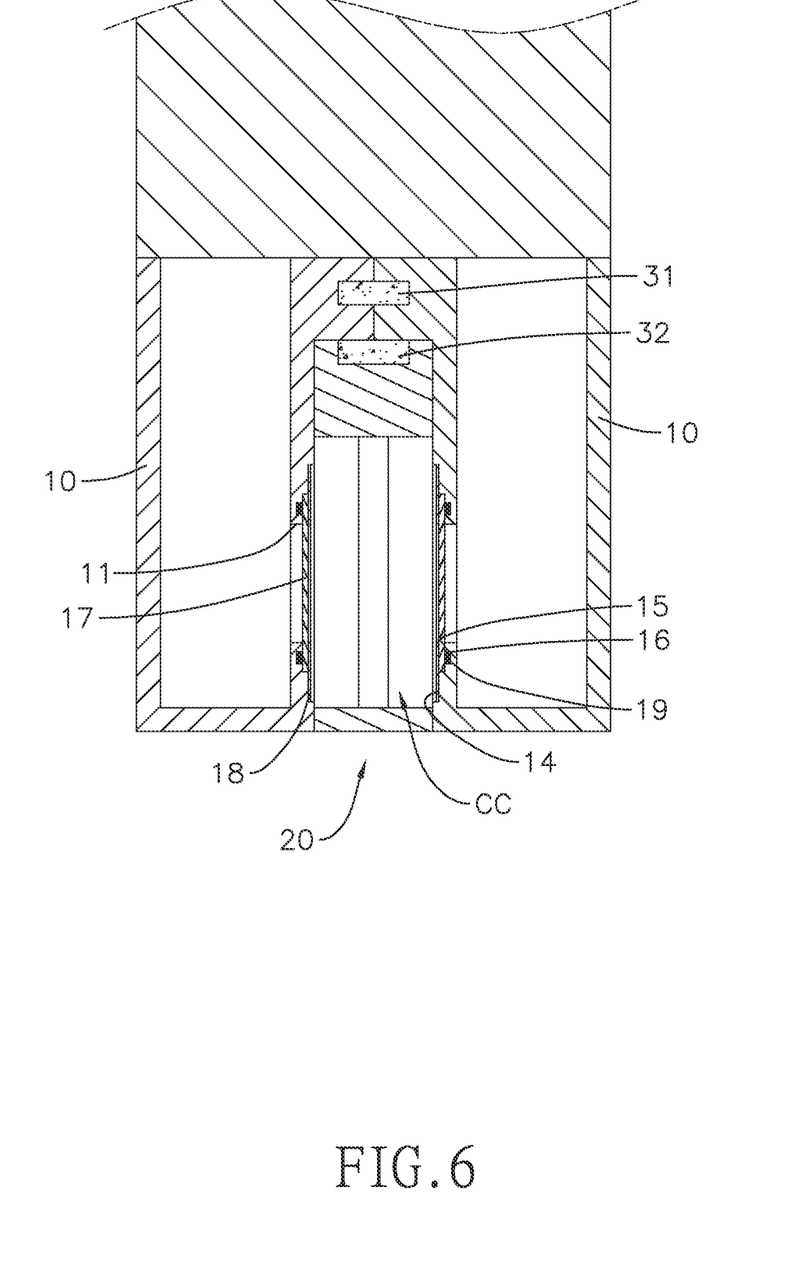
FIG. 6 anther cross-sectional side view of the examining property probe in FIG. 1, showing mounted to a detecting end of the optical water quality detection device.

With further reference to FIG. 6, the two stationary seats 10 are connected with each other to form a substantially inverted U-shaped structure. A light source module is mounted in one of the stationary seats 10 while a spectrum sensor is mounted in the other one of the stationary seats 10. Each of the stationary seats 10 has an inner sidewall 101, a through hole 11, a side protrusion 12, and a positioning protrusion 13. The inner sidewalls 101 of the two stationary seats 10 face toward each other and are disposed apart from each other, such that a detecting channel CC is formed between the inner sidewalls 101 of the two stationary seats 10. The through hole 11 is formed through the inner sidewall 101 of the stationary seat 10 and communicates with an interior of the stationary seat 10. Two glass covers 17 are mounted on the two stationary seats 10 respectively. Each of the glass covers 17 covers the through hole 11 of a respective one of stationary seats 10.

The side protrusion 12 protrudes from the inner sidewall 101 of the stationary seat 10 and is disposed adjacent to a top of the stationary seat 10. A first magnetic element 31 is partially embedded in the side protrusion 12 of one of the stationary seats 10 and is partially embedded in the side protrusion 12 of the other one of the stationary seats 10, such that the two stationary seats 10 are connected together. The positioning protrusion 13 protrudes from a bottom of the side protrusion 12 and protrudes toward the detecting channel CC.

Figure 4:
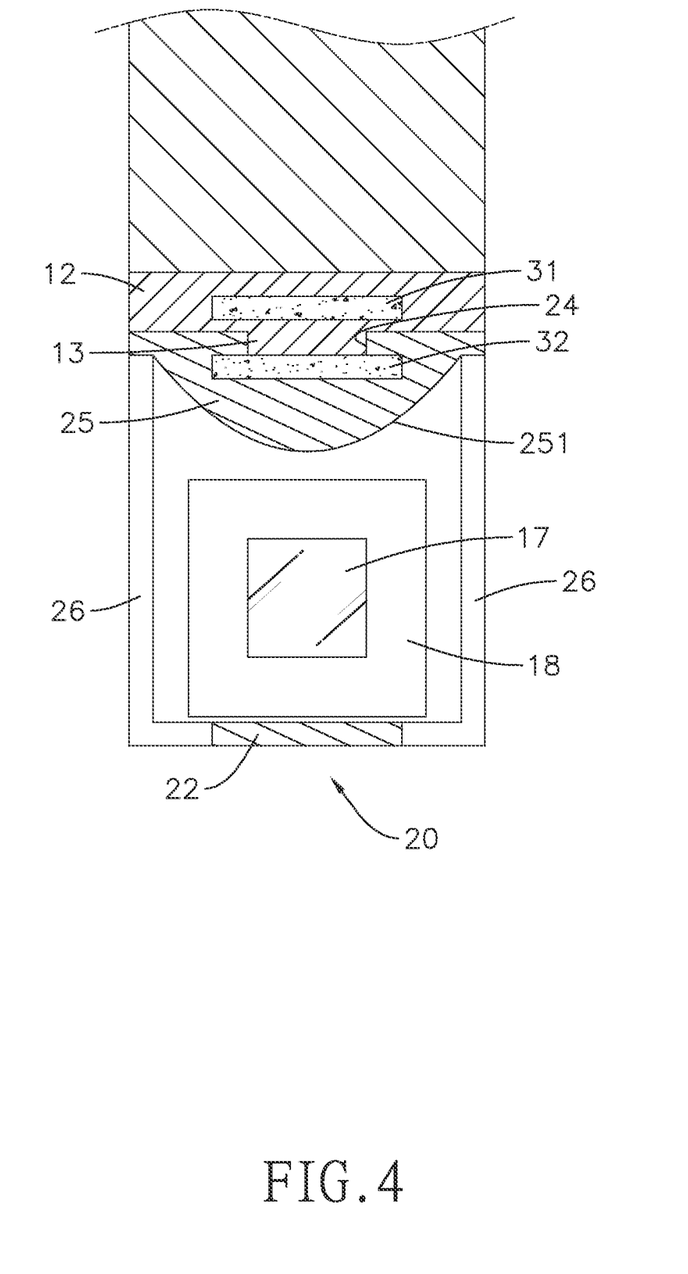
FIG. 4 is a cross-sectional side view of the examining property probe in FIG. 1, showing mounted to a detecting end of the optical water quality detection device.
Figure 5:
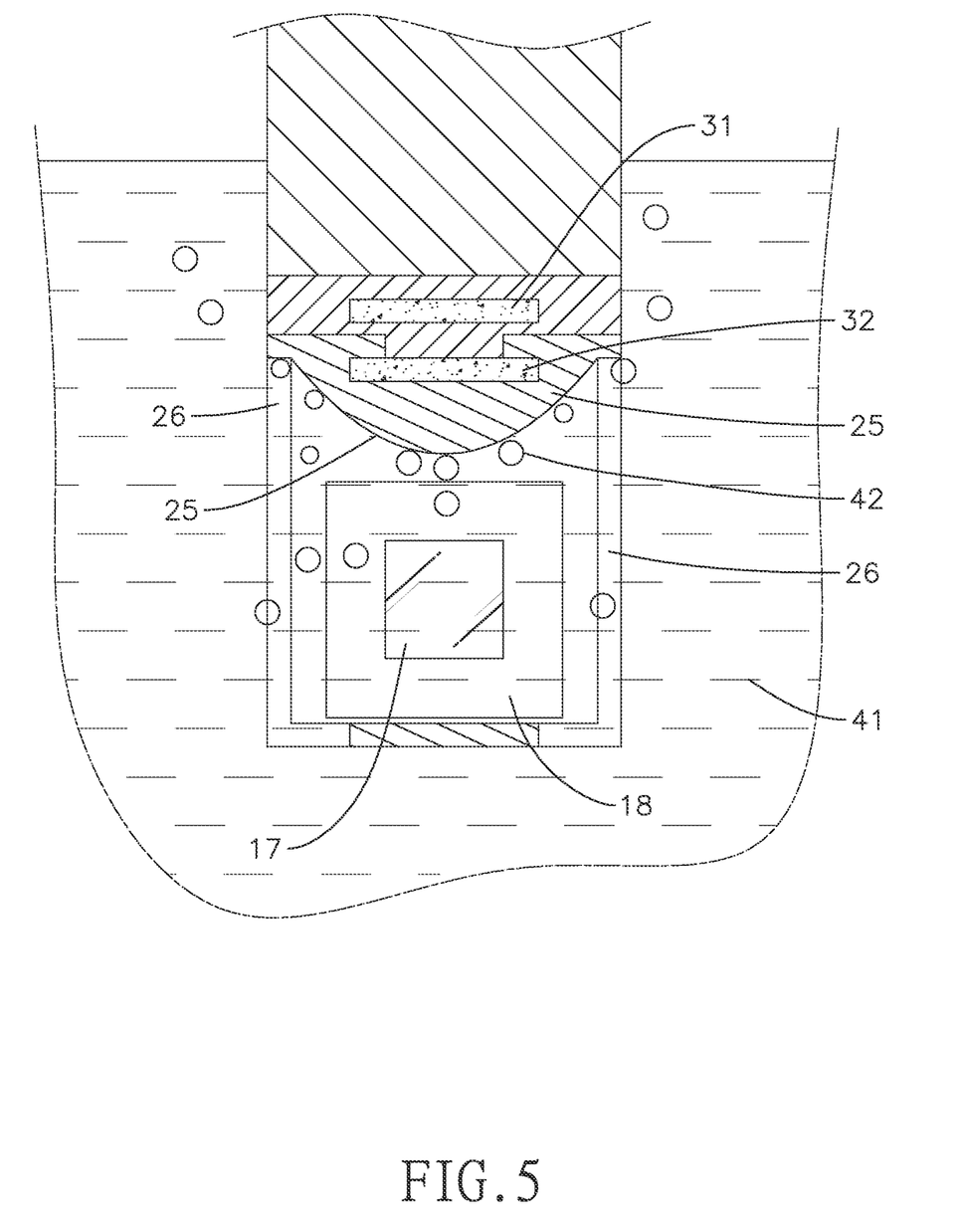
FIG. 5 is an operational cross-sectional side view of the examining property probe in FIG. 4, showing being put in a liquid to be detected.

With further reference to FIGS. 3 and 4, the fencing frame 20 is substantially annular and is detachably mounted in the detecting channel CC between the two stationary seats 10, so as to preliminarily filter the liquid 41 that flows into the detecting channel CC. The fencing frame 20 has an upper portion 21, a bottom panel 22, two side panels 23, a positioning recess 24, a guiding protrusion 25, and two elongated orifices 26.

The upper portion 21 and the bottom panel 22 of the fencing frame 20 are oppositely defined on two opposite sides of the fencing frame 20. The upper portion 21 of the fencing frame 20 abuts against the side protrusions 12 of the two stationary seats 10. The two side panels 23 are oppositely defined on another two opposite sides of the fencing frame 20.

A second magnetic element 32 is embedded in the upper portion 21 of the fencing frame 20 and corresponds in position to the first magnetic element 31. The second magnetic element 32 and the first magnetic element 31 face each other with opposite magnetic poles. Thus, when the fencing frame 20 is mounted into the detecting channel CC, the first magnetic element 31 and the second magnetic element 32 attract each other, such that the fencing frame 20 is stably set in the detecting channel CC.

The positioning recess 24 is formed in an outer surface of the upper portion 21 of the fencing frame 20. The positioning protrusions 13 of the two stationary seats 10 protrude in the positioning recess 24, so as to fix a relative position between the fencing frame 20 and the stationary seats 10. Thus, the fencing frame 20 would not be shifted when the fencing frame 20 is mounted in the detecting channel 14. Moreover, the second magnetic element 32 is embedded in a bottom defined in the positioning recess 24.

The guiding protrusion 25 protrudes from an inner side of the upper portion 21 of the fencing frame 20 and has a convex surface 251 facing toward the bottom panel 22 of the fencing frame 20. The convex surface 251 extends between the two side panels 23 along a cycloidal path and has two opposite end edges connected with the two side panels 23 respectively. The elongated orifices 26 are formed through the two side panels 23 respectively and extend to the bottom panel 22, such that each of the elongated orifices 25 is substantially L-shaped. Each of the elongated orifices 25 has an upper end connected with a respective one of the end edges of the convex surface 251 of the guiding portion 25.

Said "cycloidal path" is defined as a curve that is traced by a point on a circle as the circle rolls along a straight line without slipping. According to calculation and experiment, under the premise that there is only uniform gravitational force and no friction, releasing a stationary particle from a high point and letting the particle slide along a path to a low point, the path with the shortest travel time is said cycloidal path rather than a straight path or a curved path.

With further reference to FIG. 4, according to characteristics of said cycloidal path, when the optical water quality detection device 50 having the examining property probe 1 is put into the liquid 41 to be detected, air bubbles 42 formed and entering the detecting channel CC flow upward due to buoyance until touching the convex surface 251 of the guiding portion 25. Since the convex surface 251 extends along said cycloidal path, the convex surface 251 is helpful in guiding the air bubbles 42 to move upward along the convex surface 251 and to expel the air bubbles 42 out of the detecting channel CC from one of the elongated orifices 26 quickly. The cycloidal path has a characteristic of rapidly increasing a speed of an object sliding along the cycloidal path. Moreover, the cycloidal path on the convex surface 251 in the fencing frame 20 is a reversed cycloid and has the original perfect curve of the cycloid (the most perfect slope for speed and distance). Therefore, the convex surface 251 can strike a balance between smoothness and final speed, so as to provide a stronger force for expelling the air bubbles 42, allowing the air bubbles 42 to slide out of the fencing frame 20 smoothly with obstruction.

With reference to FIGS. 3 and 6, the inner sidewall 101 of each of the stationary seats 10 is further provided with an outer recess 14, an inner recess 15, and a glue groove 16. The outer recess 14 is formed in the inner sidewall 101 of the stationary seat 10. The inner recess 15 is formed in a bottom defined in the outer recess 14. Said through hole 11 is formed through a bottom defined in the inner recess 15. The glue groove 16 is formed in the bottom defined in the inner recess 15, is disposed around the through hole 11, and is filled with glue 19.

Each of the glass covers 17 is embedded and secured in the inner recess 15 of a respective one of the stationary seats 10 via the glue 19, and covers the through hole 11 of the respective one of the stationary seats 10. Preferably, the glass cover 17 flushes with the bottom defined in the outer recess 14 of the respective one of the stationary seats 10. Two nameplates 18 are mounted onto the stationary seats 10 respectively. Each of the nameplates 18 is annular and is embedded and secured in the outer recess 14 of a respective one of the stationary seats 10, and covers a connection portion between a peripheral edge of a respective one of the glass covers 17 and the respective one of the stationary seats 10.

Since the glue 19 is filled in the glue groove 16, the glass cover 17 is able to abut against the bottom defined in the inner recess 15, so as to prevent the liquid 41 outside to seep into the interiors of the stationary seats 10 and to provide good waterproof effect. Moreover, the nameplates 18 covering the connection portions between the peripheral edges of the glass covers 17 and the stationary seats 10, the liquid 41 is stopped from flowing through the connection portion between the peripheral edge of the glass cover 17 and the stationary seat 10 in advance, so as to enhance the good waterproof effect.

Furthermore, each of the glass covers 17 has an outer surface and an inner surface oppositely defined on the glass cover 17. The outer surface of the glass cover 17 faces the detecting channel CC and is coated with a hydrophobic film. The hydrophobic film makes it difficult for sewage to attach onto the outer surface of the glass cover 17, so as to prevent the glass cover 17 from being dirtied. The inner surface of the glass cover 17 faces the interior of the stationary seat 10 and is coated with a hydrophilic film. The hydrophilic film allows water molecules to be evenly distributed on the inner surface of the glass cover 17 before forming water droplets, so as to prevent the glass cover 17 from fogging up.

The examining property probe 1 of the present invention has the following advantages. The cycloidal path on the convex surface 251 in the fencing frame 20, with its structural design, assists in guiding the air bubbles stuck in the detecting channel CC to leave the detecting channel CC without vibrating the examining property probe 1. Since the air bubbles 41 do not remain in the detecting channel CC, the spectral information is not affected.

Moreover, with the hydrophobic film coated on the outer surface of each of the glass covers 17 and the hydrophilic film coated on the inner surface of each of the glass covers 17, the glass covers 17 are not dirtied or fogged up. Accordingly, the light beam is not obstructed by dirt or fog and the optical water quality detection device 50 having the examining property probe 1 is able to provide correct result regarding the components in the liquid 41 to be detected.

In addition, with the glue 19 filled in the glue groove 16, the glass cover 17 is able to abut against the bottom defined in the inner recess 15, so as to prevent the liquid 41 to seep into the interiors of the stationary seats 10 and to provide good waterproof effect.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. An optical water quality detection device comprising an examining property probe, the examining property probe comprising:

two stationary seats connected with each other, each of the stationary seats having an inner sidewall, and the inner sidewalls of the two stationary seats facing toward each other and disposed apart from each other, wherein a detecting channel is formed between the inner sidewalls of the two stationary seats; and a fencing frame being annular and detachably mounted in the detecting channel between the two stationary seats, and the fencing frame having: an upper portion; a bottom panel; two side panels; a guiding protrusion protruding from an inner side of the upper portion of the fencing frame and having a convex surface facing toward the bottom panel of the fencing frame, wherein the convex surface extends between the two side panels along a cycloidal path and has two opposite end edges connected with the two side panels respectively; and two elongated orifices formed through the two side panels respectively and extending to the bottom panel, and each of the elongated orifices having an upper end connected with a respective one of the end edges of the convex surface of the guiding portion.

2. The optical water quality detection device as claimed in claim 1, wherein each of the stationary seats has: a through hole formed through the inner sidewall of the stationary seat and communicating with an interior of the stationary seat; an outer recess formed in the inner sidewall of the stationary seat; an inner recess formed in a bottom defined in the outer recess, wherein said through hole is formed through a bottom defined in the inner recess; and a glue groove formed in the bottom defined in the inner recess, disposed around the through hole, and filled with glue; and two glass covers are mounted on the two stationary seats respectively, and each of the glass covers is embedded and secured in the inner recess of a respective one of the stationary seats via the glue and covers the through hole of the respective one of the stationary seats.

3. The optical water quality detection device as claimed in claim 2, wherein the glass cover flushes with the bottom defined in the outer recess of the respective one of the stationary seats.

4. The optical water quality detection device as claimed in claim 3, wherein the glass cover has: an outer surface facing the detecting channel and coated with a hydrophobic film; and an inner surface facing the interior of the stationary seat and coated with a hydrophilic film.

5. The optical water quality detection device as claimed in claim 4, wherein each of the stationary seats has a side protrusion protruding from the inner sidewall of the stationary seat and disposed adjacent to a top of the stationary seat, wherein a first magnetic element is partially embedded in the side protrusion of one of the stationary seats and is partially embedded in the side protrusion of the other one of the stationary seats; and a second magnetic element is embedded in the upper portion of the fencing frame and corresponds in position to the first magnetic element; and the second magnetic element and the first magnetic element face each other with opposite magnetic poles.

6. The optical water quality detection device as claimed in claim 4, wherein: each of the stationary seats has a positioning protrusion protruding from a bottom of the side protrusion and protruding toward the detecting channel;

the fencing frame has a positioning recess formed in an outer surface of the upper portion of the fencing frame; and the positioning protrusions of the two stationary seats protrude in the positioning recess.

7. The optical water quality detection device as claimed in claim 3, wherein each of the stationary seats has a side protrusion protruding from the inner sidewall of the stationary seat and disposed adjacent to a top of the stationary seat, wherein a first magnetic element is partially embedded in the side protrusion of one of the stationary seats and is partially embedded in the side protrusion of the other one of the stationary seats; and a second magnetic element is embedded in the upper portion of the fencing frame and corresponds in position to the first magnetic element; and the second magnetic element and the first magnetic element face each other with opposite magnetic poles.

8. The optical water quality detection device as claimed in claim 3, wherein: each of the stationary seats has a positioning protrusion protruding from a bottom of the side protrusion and protruding toward the detecting channel; the fencing frame has a positioning recess formed in an outer surface of the upper portion of the fencing frame; and the positioning protrusions of the two stationary seats protrude in the positioning recess.

9. The optical water quality detection device as claimed in claim 2, wherein the glass cover has: an outer surface facing the detecting channel and coated with a hydrophobic film; and an inner surface facing the interior of the stationary seat and coated with a hydrophilic film.

10. The optical water quality detection device as claimed in claim 9, wherein
each of the stationary seats has a side protrusion protruding from the inner sidewall of the stationary seat and disposed adjacent to a top of the stationary seat, wherein a first magnetic element is partially embedded in the side protrusion of one of the stationary seats and is partially embedded in the side protrusion of the other one of the stationary seats; and
a second magnetic element is embedded in the upper portion of the fencing frame and corresponds in position to the first magnetic element; and the second magnetic element and the first magnetic element face each other with opposite magnetic poles.

11. The optical water quality detection device as claimed in claim 9, wherein: each of the stationary seats has a positioning protrusion protruding from a bottom of the side protrusion and protruding toward the detecting channel; the fencing frame has a positioning recess formed in an outer surface of the upper portion of the fencing frame; and the positioning protrusions of the two stationary seats protrude in the positioning recess.

12. The optical water quality detection device as claimed in claim 2, wherein
each of the stationary seats has a side protrusion protruding from the inner sidewall of the stationary seat and disposed adjacent to a top of the stationary seat, wherein a first magnetic element is partially embedded in the side protrusion of one of the stationary seats and is partially embedded in the side protrusion of the other one of the stationary seats; and
a second magnetic element is embedded in the upper portion of the fencing frame and corresponds in position to the first magnetic element; and the second magnetic element and the first magnetic element face each other with opposite magnetic poles.

13. The optical water quality detection device as claimed in claim 2, wherein: each of the stationary seats has a positioning protrusion protruding from a bottom of the side protrusion and protruding toward the detecting channel; the fencing frame has a positioning recess formed in an outer surface of the upper portion of the fencing frame; and the positioning protrusions of the two stationary seats protrude in the positioning recess.

14. The optical water quality detection device as claimed in claim 1, wherein
each of the stationary seats has a side protrusion protruding from the inner sidewall of the stationary seat and disposed adjacent to a top of the stationary seat, wherein a first magnetic element is partially embedded in the side protrusion of one of the stationary seats and is partially embedded in the side protrusion of the other one of the stationary seats; and
a second magnetic element is embedded in the upper portion of the fencing frame and corresponds in position to the first magnetic element; and the second magnetic element and the first magnetic element face each other with opposite magnetic poles.

15. The optical water quality detection device as claimed in claim 1, wherein: each of the stationary seats has a positioning protrusion protruding from a bottom of the side protrusion and protruding toward the detecting channel; the fencing frame has a positioning recess formed in an outer surface of the upper portion of the fencing frame; and the positioning protrusions of the two stationary seats protrude in the positioning recess.

* * * * *